United States Patent [19]

Magnuson

[11] Plant 4,644

[45] Feb. 10, 1981

[54] PEACH TREE

[75] Inventor: Darryl P. Magnuson, Kingsburg, Calif.

[73] Assignee: Richland Sales Co., Reedley, Calif.

[21] Appl. No.: 83,120

[22] Filed: Oct. 9, 1979

[51] Int. Cl.[3] ..... A01H 5/03

[52] U.S. Cl. ..... Plt./43

[58] Field of Search ..... Plt./43

*Primary Examiner*—Robert E. Bagwill

*Attorney, Agent, or Firm*—Roger B. Webster

[57] ABSTRACT

A peach tree which is of medium size, medium vigor, spreading, dense, vase-formed, hardy, foliated with medium size, oval-lanceolate, acutely pointed leaves, blooms with large, pink flowers, and is a regular and very productive bearer of medium-large size, globose, freestone fruit having apricot skin substantially overspread with dark red, and yellow flesh with red streaked and mottled into the flesh from the pit cavity.

1 Drawing Figure

BACKGROUND OF THE VARIETY:

1. Field of the Discovery

The present new and distinct variety of peach tree is embraced by Class 43, Plants, of the United States Patent Office Manual of Classification.

2. Prior Varieties

Among the existent varieties of peach trees which are known to me, I make particular reference to the O'-Henry (U.S. Plant Pat. No. 2,964)—mentioned hereinafter in this specification.

ORIGIN OF THE VARIETY

The present variety of peach tree was discovered by me while harvesting an orchard of peaches of the O'-Henry variety growing on my ranch located at 15839 East Rose, Kingsburg, Fresno County, Calif.; the variety having been first noticed apparently as a bud sport limb growing on a tree of the O'Henry variety, and which limb bore fruit which ripened substantially later than the other fruit in such orchard. Upon my discovery of such individually distinct limb, and recognizing its possible commercial value as a new and distinct variety, I determined to effect asexual reproduction thereof.

ASEXUAL REPRODUCTION OF THE VARIETY

The present variety of peach tree was asexually reproduced, on my behalf and by a commercial nursery, by budding, and such asexual reproductions—in maturity—ran true to the original bud sport limb in all respects.

SUMMARY OF THE VARIETY

The herein-claimed variety of peach tree is of medium size, medium vigor, spreading, dense, vase-formed, hardy, foliated with medium size, oval-lanceolate, acutely pointed leaves, blooms with large, pink flowers, and is a regular and very productive bearer of medium-large size, globose, freestone fruit having apricot skin substantially overspread with dark red, and yellow flesh with red streaked and mottled into the flesh from the pit cavity.

The herein-claimed variety of peach tree—while having general similarity to the O'Henry variety in tree and fruit—is distinctively characterized by a ripening period approximately ten days after completion of the harvest of said O'Henry variety.

BRIEF DESCRIPTION OF THE DRAWING

The drawing is an illustration, by photographic reproduction in color, of a number of separate fruit; one such fruit being cut into halves, with the stone remaining in one half.

DESCRIPTION OF THE VARIETY

The botanical details of this new and distinct variety of peach tree—with color definitions (except those in common color terms) referenced to Maerz and Paul Dictionary of Color—are as follows:

Tree:
- *Size.*—Medium.
- *Vigor.*—Medium.
- *Growth.*—Spreading.
- *Density.*—Dense.
- *Form.*—Vase-formed.
- *Hardiness.*—Hardy.
- *Production.*—Very productive.
- *Bearing.*—Regular bearer.

Trunk:
- *Size.*—Medium.
- *Texture.*—Medium.

Branches:
- *Size.*—Medium.
- *Texture.*—Smooth.
- *Color.*—Brown (7-C-12).
- *Lenticels.*—Number—Medium. Size—Medium.

Leaves:
- *Size.*—Medium. Average length—150 mm. Average width—35 mm.
- *Shape.*—Oval—lanceolate. Acutely pointed.
- *Thickness.*—Medium.
- *Color.*—Top Side—Dark green (23-J-7) Under Side—Lighter green (23-J-4).
- *Margin.*—Finely serrate.
- *Petiole.*—Medium length (average—10 mm.) Medium thickness (average—2 mm.).
- *Glands.*—Average number—3. Alternate Small (0.5 mm. × 1.0 mm.). Mixed. Green (17-J-7). Positioned usually 1 on petiole, and 2 on leaf blade.

Flower buds:
- *Hardiness.*—Hardy.
- *Size.*—Large.

*Length.*—Long.
*Form.*—Obtuse. Plump. Free.
*Pubescence.*—Pubescent.

Flowers:
*Blooming period.*—Date of first bloom—Mar. 5th. Date of full bloom—Mar. 11th. Medium, as compared with other varieties.
*Size.*—Large (diameter—40 mm. when open).
*Color.*—Upper side—Pink (49-D-1). Lower side—Pink (49-E-1).
*Stamens.*—Average number—40-42.

Fruit:
*Maturity when described.*—Hard.
*Date of first picking.*—Aug. 22nd.
*Date of last picking.*—Sept. 1st.
*Size.*—Uniform. Medium—large. Average diameter axially—75 mm. Average transversely in suture plane—78 mm.
*Form.*—Unsymmetrical. Globose. Oblate. Compressed laterally.
*Suture.*—Distinct. Extends from base to beyond but discontinuous at apex. Slight depression beyond pistil point.
*Ventral surface.*—Rounded slightly.
*Lips.*—Equal.
*Cavity.*—Flaring. Average depth—13 mm. Average breadth—25 mm.
*Base.*—Rounded.
*Apex.*—Depressed.
*Pistil point.*—Apical.

Skin:
*Thickness.*—Thin.
*Texture.*—Medium.
*Flavor.*—Astringent.
*Tenacity.*—Tenacious to flesh.
*Tendency to crack.*—Slight.
*Down.*—Scant. Does not roll up when rubbed.
*Color.*—Ground color—Apricot (10-I-7). Blush color—Dark red (6-L-10).

Flesh:
*Color.*—Yellow (10-J-5) with red (7-L-9) streaked and mottled into the flesh from the pit cavity. Surface of pit cavity—Red (7-L-9) with white fibers.
*Juice.*—Moderate.

*Texture.*—Firm. Fine. Meaty.
*Fibers.*—Few. Fine.
Ripens.—Evenly.
*Flavor.*—Subacid. Delicate.
*Aroma.*—Distinct.
*Eating quality*—Good.

Stone
*Type.*—Free.
*Fibers.*—Short.
*Parting from flesh*—Smoothly.
*Retention of fibers.*—Retains short fiber-like threads along ridges.
*Size.*—Medium—large. Average length—38 mm. Average breadth—30 mm. Average thickness—20 mm.
*Form.*—Oval.
*Base.*—Straight.
*Hilum.*—Narrow. Oblong.
*Apex.*—Acuminate.
*Sides.*—Unequal. Flattened on right side.
*Surface.*—Regularly furrowed throughout. Ridged throughout. Pitted throughout.
*Ridges.*—Jagged toward base.
*Pits.*—Elongated.
*Ventral edge.*—Thin, with wing toward base.
*Dorsal edge.*—Full, with deep, broad groove throughout.
*Color.*—Coffee (15-A-11).
*Tendency to split.*—Slight.

Use: Market.
Keeping Quality: Good.
Resistance to insects and diseases: Good.
Shipping Quality: Good.

The peach tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, which is generally similar, in tree and fruit, to the O'Henry variety, but distinctively characterized by a ripening period approximately ten days later.

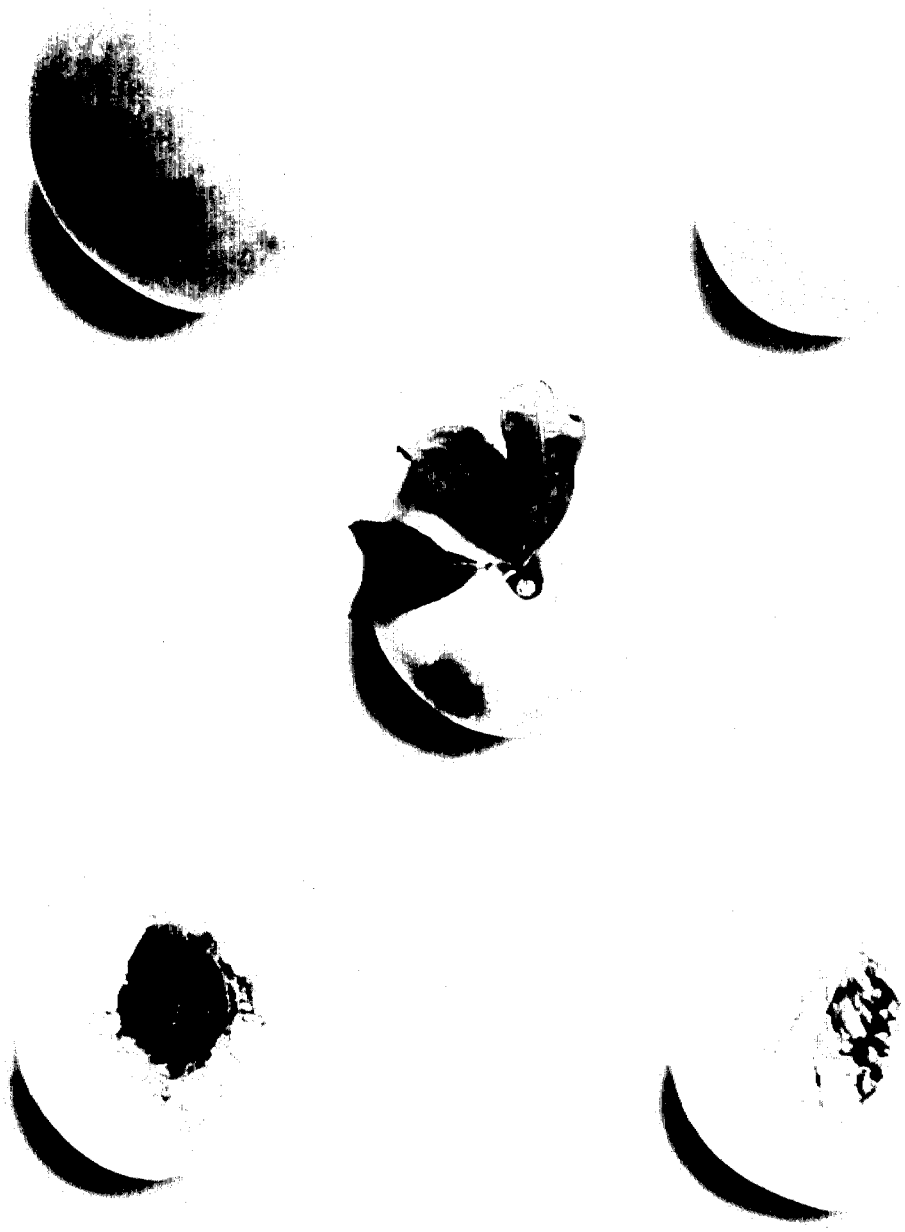

* * * * *